US010444539B2

(12) United States Patent
Liang (10) Patent No.: US 10,444,539 B2
(45) Date of Patent: Oct. 15, 2019

(54) METHODS AND SYSTEMS FOR DETERMINING REFRACTIVE CORRECTIONS OF HUMAN EYES FOR EYEGLASSES

(71) Applicant: PERFECT VISION TECHNOLOGY (HK) LTD., Tsuen Wan (HK)

(72) Inventor: Junzhong Liang, Fremont, CA (US)

(73) Assignee: PERECT VISION TECHNOLOGY (HK) LTD., Tsuen Wan (HK)

( * ) Notice: Subject to any disclaimer, the term of this patent is extended or adjusted under 35 U.S.C. 154(b) by 137 days.

(21) Appl. No.: 15/631,935

(22) Filed: Jun. 23, 2017

(65) Prior Publication Data
US 2017/0329154 A1  Nov. 16, 2017

Related U.S. Application Data

(63) Continuation of application No. PCT/US2017/030784, filed on May 3, 2017, which is (Continued)

(51) Int. Cl.
*A61B 3/02* (2006.01)
*G02C 7/02* (2006.01)
(Continued)

(52) U.S. Cl.
CPC ............ *G02C 7/027* (2013.01); *A61B 3/0033* (2013.01); *A61B 3/0285* (2013.01); *A61B 3/103* (2013.01);
(Continued)

(58) Field of Classification Search
CPC ... A61B 3/0025; A61B 3/0285; A61B 3/1015; A61B 3/103; A61B 3/0033; A61B 3/185;
(Continued)

(56) References Cited

U.S. PATENT DOCUMENTS 2,021,812 A  11/1935 Scott
3,431,688 A  3/1969 Rudd et al.
(Continued)

FOREIGN PATENT DOCUMENTS

CN  2031935  2/1989
CN  1781443 A  6/2006
(Continued)

OTHER PUBLICATIONS

International Search Report and Written Opinion dated Jul. 11, 2017 for PCT Patent Application No. PCT/US2017/030784.
Office Action dated Jan. 25, 2018 for U.S. Appl. No. 15/151,491.

*Primary Examiner* — Brandi N Thomas
(74) *Attorney, Agent, or Firm* — MLO, a professional corp.

(57) ABSTRACT

Methods, devices, and systems are disclosed for determining refractive corrections of human eyes to reduce and eliminate image distortion associated with eyeglasses. In some embodiments, an objective refraction module is configured to measure refractive errors of an eye objectively, without subjective feedback from a tested subject. A computation module is configured to generate a plurality of objective prescriptions. A phoropter module is configured to perform a subjective refraction for determining a plurality of subjective spherical powers based on the plurality of objective prescriptions. An output module is configured to generate a plurality of prescriptions for eyeglasses, the plurality of prescriptions comprising (a) a first prescription having a first subjective spherical power $f_{s1}$, a first objective cylinder power $F_{c1}$, and a first objective cylinder angle $F_{a1}$, and (b) a second prescription having a second subjective spherical power $f_{s2}$, a second objective cylinder power $F_{c2}$, and a second objective cylinder angle $F_{a2}$.

23 Claims, 7 Drawing Sheets

Related U.S. Application Data a continuation-in-part of application No. 15/151,491, filed on May 11, 2016, now abandoned.

(51) Int. Cl.
    *A61B 3/10*     (2006.01)
    *A61B 3/028*     (2006.01)
    *A61B 3/18*     (2006.01)
    *A61B 3/00*     (2006.01)
    *A61B 3/103*     (2006.01)

(52) U.S. Cl.
    CPC ............ *A61B 3/1015* (2013.01); *A61B 3/185* (2013.01); *G02C 2202/22* (2013.01)

(58) Field of Classification Search
    CPC ........... A61B 3/036; A61B 3/18; A61B 3/032; A61B 3/0058; A61B 3/0083; A61B 3/152; A61B 3/0041; A61B 3/0325; A61B 3/028; A61B 3/1035; A61B 3/113; A61B 3/14
    USPC ........ 351/200, 205–206, 210, 216, 221–223, 351/232, 236
    See application file for complete search history.

(56) References Cited

U.S. PATENT DOCUMENTS

| | | | |
|---|---|---|---|
| 5,434,707 A | 7/1995 | Dalzell et al. | |
| 5,652,638 A | 7/1997 | Roffman et al. | |
| 5,777,719 A | 7/1998 | Williams et al. | |
| 6,142,625 A | 11/2000 | Sawano et al. | |
| 8,214,265 B2 | 7/2012 | Peters | |
| 8,219,466 B2 | 7/2012 | Gui et al. | |
| 8,229,806 B1 | 7/2012 | Chapman et al. | |
| 8,235,247 B2 | 8/2012 | Alvarez | |
| 8,276,735 B2 | 10/2012 | Georgens | |
| 8,419,185 B2 | 4/2013 | Liang | |
| 8,827,448 B2 | 9/2014 | Liang | |
| 9,277,863 B2 | 3/2016 | Liang | |
| 2004/0054358 A1 | 3/2004 | Cox et al. | |
| 2004/0263786 A1 | 12/2004 | Williams et al. | |
| 2005/0200809 A1 | 9/2005 | Dreher et al. | |
| 2006/0023163 A1 | 2/2006 | Foster | |
| 2006/0203198 A1 | 9/2006 | Liang | |
| 2006/0235369 A1 | 10/2006 | Macrae et al. | |
| 2006/0279699 A1 | 12/2006 | Liang | |
| 2007/0159593 A1 | 7/2007 | Hibino et al. | |
| 2008/0018855 A1 | 1/2008 | Larichev et al. | |
| 2008/0126809 A1 | 5/2008 | Rothschild | |
| 2008/0143960 A1 | 6/2008 | MacRae | |
| 2008/0143963 A1 | 6/2008 | Lindacher | |
| 2008/0198328 A1 | 8/2008 | Seriani et al. | |
| 2009/0128901 A1 | 5/2009 | Tilleman et al. | |
| 2009/0244480 A1 | 10/2009 | De Gaudemaris et al. | |
| 2009/0323020 A1 | 12/2009 | Zhao et al. | |
| 2010/0039614 A1 | 2/2010 | Morris et al. | |
| 2010/0074477 A1 | 3/2010 | Fujii et al. | |
| 2010/0265463 A1 | 10/2010 | Lai | |
| 2010/0283963 A1 | 11/2010 | Giraudet et al. | |
| 2011/0228225 A1 | 9/2011 | Liang | |
| 2012/0253837 A1 | 10/2012 | Cashman et al. | |
| 2012/0271412 A1 | 10/2012 | Feingold et al. | |
| 2013/0100410 A1* | 4/2013 | Liang ...................... | A61B 3/18 351/223 |
| 2013/0135586 A1 | 5/2013 | Lai et al. | |
| 2014/0368795 A1 | 12/2014 | Liang | |
| 2015/0305619 A1 | 10/2015 | Liang | |
| 2017/0329154 A1 | 11/2017 | Liang | |

FOREIGN PATENT DOCUMENTS

| | | |
|---|---|---|
| GB | 1463107 A | 2/1977 |
| JP | S54131950 | 10/1979 |
| JP | S601604 A | 1/1985 |
| JP | H03229212 | 10/1991 |
| JP | H05332720 A | 12/1993 |
| JP | H06034920 | 2/1994 |
| JP | H0915541 A | 1/1997 |
| JP | H10175149 A | 6/1998 |
| JP | 11056779 A | 3/1999 |
| JP | H11267100 A | 10/1999 |
| JP | H11295668 | 10/1999 |
| JP | 2002156611 | 5/2002 |
| JP | 2003140094 | 5/2003 |
| JP | 2006517135 A | 7/2006 |
| JP | 2007240553 A | 9/2007 |
| JP | 2009521726 A | 6/2009 |
| JP | 2006178245 A | 7/2017 |
| WO | 2005040896 A1 | 5/2005 |
| WO | 2007075975 A2 | 7/2007 |
| WO | 2008049503 A2 | 5/2008 |
| WO | 2009123700 A | 10/2009 |
| WO | 2010065475 A2 | 6/2010 |
| WO | 2012054651 A2 | 4/2012 |
| WO | 2014085352 A1 | 6/2014 |

\* cited by examiner

METHODS AND SYSTEMS FOR DETERMINING REFRACTIVE CORRECTIONS OF HUMAN EYES FOR EYEGLASSES

RELATED APPLICATIONS

This application 1) is a continuation of International Patent Application No. PCT/US17/30784, filed on May 3, 2017 and entitled "Methods and Systems for Determining Refractive Corrections of Human Eyes for Eyeglasses"; which claims priority from 2) U.S. patent application Ser. No. 15/151,491, filed May 11, 2016, and entitled "Methods and Systems for Determining Refractive Corrections of Human Eyes for Eyeglasses; all of which are hereby incorporated by reference for all purposes.

BACKGROUND OF THE INVENTION

Consumers often have to adapt to a new pair of eyeglasses which is a known issue in the eyeglasses industry. It often relates to image distortion of the new eyeglasses, and adaptation to new eyeglasses can sometimes be a very painful process for some people. Three consequences happen when the image distortion by eyeglasses is not handled properly. First, a pair of new eyeglasses may take 1 to 2 week(s) for consumers to get used to, with the individual's experience varying from person to person. Second, a significant portion of new eyeglasses purchased are abandoned because consumers can never become accustomed to them. This causes monetary losses because a new pair of eyeglasses does improve an individual's vision, and getting used to the new eyeglasses is considered a personal responsibility. Third, a population of people abandon eyeglasses all together if they fail to get used to all eyeglasses from different eyeglass shops.

Figure 1:
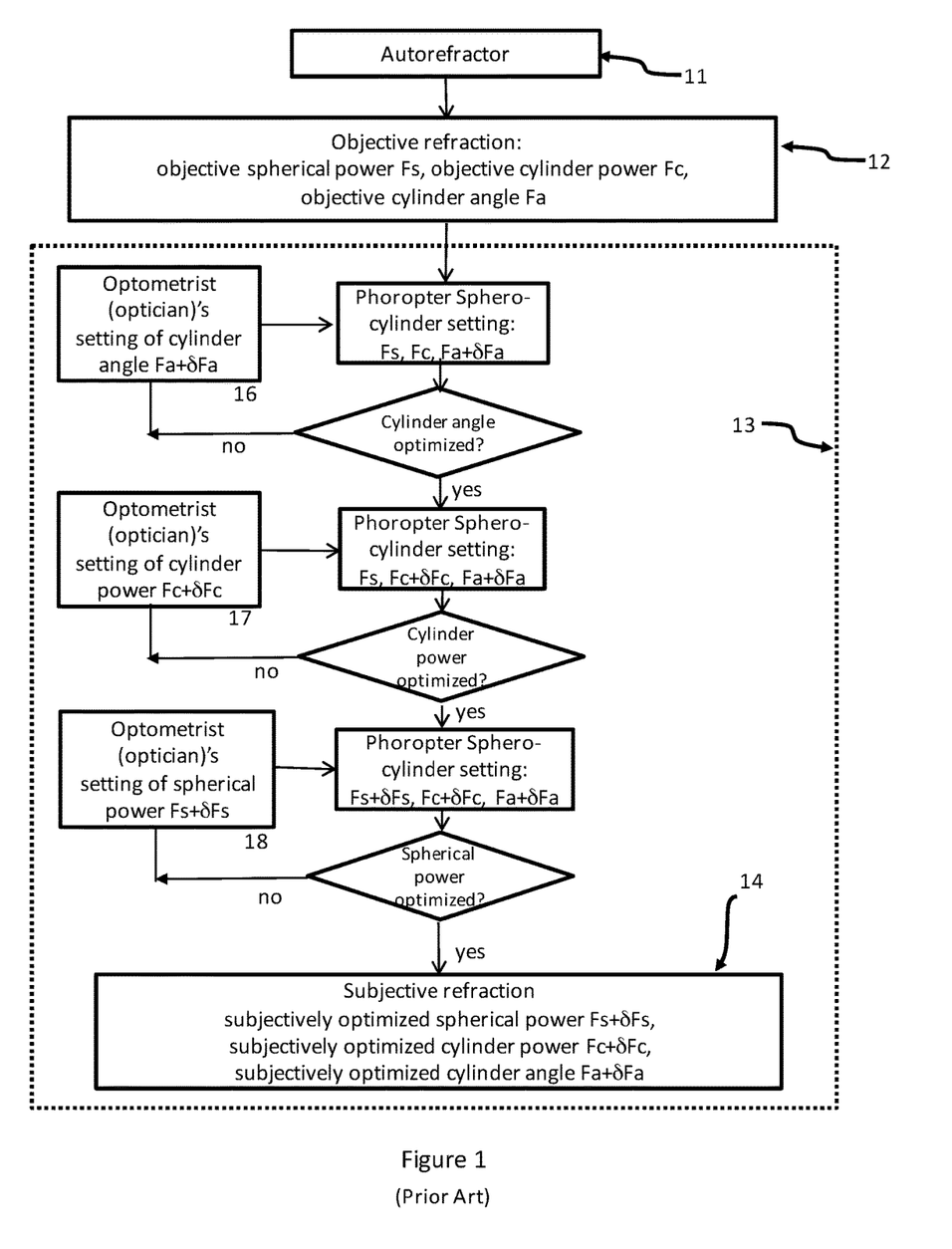
FIG. 1 shows a flowchart for a conventional method of determining refractive prescription of eyeglasses known in the art.

The conventional refraction process shown in FIG. 1 relies on experience and skills of an individual optometrist (optician) to set a starting point as well as an ending point for the prescription of eyeglasses. First, an autorefractor 11 is typically used to get an objective measurement of an eye's refractive errors and provide a rough objective prescription 12 including a spherical power $F_s$, a cylinder power $F_c$ and a cylinder angle $F_a$. Second, an optometrist (or an optician) will determine a rough spherical correction in a phoropter 13, and then administrates a subjective optimization of spherical power, cylinder power and cylinder angle based on the objective prescription. The subjective optimization is based on the experience and skill of the optometrist or optician, and on subjective feedback of the tested subjects (i.e., the patient). In step 16 of subjective refraction, the cylinder angle is subjectively optimized by letting the tested subject first see an astigmatism chart and then an acuity chart afterwards. The optometrist (an optician) will set/modify the cylinder angle based on the objective prescription as well as feedback of the tested subject. In step 17 of subjective refraction, the cylinder power is subjectively optimized by having the tested subject view an acuity chart, and an optometrist (an optician) will set/modify the cylinder power based on the objective prescription as well as feedback of the tested subject. In step 18 of subjective refraction, the spherical power is subjectively optimized by letting the tested subject see an acuity chart, and an optometrist (an optician) will set/modify the spherical power based on feedback of the tested subject. The same process is repeated for the other eye of the tested subject. Third, a final prescription of the eyeglasses (subjective refraction 14) is determined for each eye with the subjectively optimized spherical power $F_s$, subjectively optimized cylinder power $F_c$, and subjectively optimized cylinder angle $F_a$. This conventional method of refraction does serve the purpose of improving vision with the new pair of eyeglasses. However, it is a different matter whether the tested subject will like the improved vision with the new pair of eyeglasses purchased.

Consequently, although many configurations and methods for vision correction are known in the art, there is a need to provide improved methods and devices to reduce and eliminate image distortion associated with eyeglasses.

SUMMARY OF THE INVENTION

In some embodiments, a method for determining refractive prescription for eyeglasses is provided. An objective refraction device is used to measure refractive errors of an eye of a tested subject objectively, where the objective refraction device excludes subjective feedback from the tested subject. A plurality of objective prescriptions for the tested subject is generated from the refractive errors of the eye measured objectively. The plurality of objective prescriptions includes (i) a first objective prescription having a first objective spherical power $F_{s1}$, a first objective cylinder power $F_{c1}$, and a first objective cylinder angle $F_{a1}$, and (ii) a second objective prescription having a second objective spherical power $F_{s2}$, a second objective cylinder power $F_{c2}$, and a second objective cylinder angle $F_{a2}$. The first objective cylinder power $F_{c1}$ and the first objective cylinder angle $F_{a1}$ of the first objective prescription are optimized for image quality, and the second objective cylinder power $F_{c2}$ and the second objective cylinder angle $F_{a2}$ of the second objective prescription are determined for a reduced image quality compared to that of the first objective prescription, or for obtaining reduced magnification differences at different orientations. A phoropter is used to perform a subjective refraction to determine a plurality of subjective spherical powers. The plurality of subjective spherical powers includes a first subjective spherical power $f_{s1}$ and a second subjective spherical power $f_{s2}$. The phoropter has a plurality of spherical lenses and cylindrical lenses, where control of the cylindrical lenses is based only on the plurality of objective prescriptions. The subjective refraction requires subjective feedback from the tested subject reading a chart through the phoropter. A plurality of prescriptions for eyeglasses is generated from the plurality of objective prescriptions and the subjective refraction. The plurality of prescriptions for eyeglasses includes (a) a first prescription having the first subjective spherical power $f_{s1}$, the first objective cylinder power $F_{c1}$, and the first objective cylinder angle $F_{a1}$, and (b) a second prescription having the second subjective spherical power $f_{s2}$, the second objective cylinder power $F_{c2}$, and the second objective cylinder angle $F_{a2}$.

In some embodiments, a system for determining refractive prescription for eyeglasses includes an objective refraction module and a computation module. The objective refraction module is configured to measure refractive errors of an eye of a tested subject objectively, without subjective feedback from the tested subject. The computation module is configured to generate a plurality of objective prescriptions for the tested subject from the refractive errors of the eye measured objectively. The plurality of objective prescriptions includes (i) a first objective prescription having a first objective spherical power $F_{s1}$, a first objective cylinder power $F_{c1}$, and a first objective cylinder angle $F_{a1}$, and (ii) a second objective prescription having a second objective spherical power $F_{s2}$, a second objective cylinder power $F_{c2}$, and a second objective cylinder angle $F_{a2}$. The first objective cylinder power $F_{c1}$ and the first objective cylinder angle $F_{a1}$ of the first objective prescription are optimized for image quality, while the second objective cylinder power $F_{c2}$ and the second objective cylinder angle $F_{a2}$ of the second objective prescription are determined for a reduced image quality compared to that of the first objective prescription, or for obtaining reduced magnification differences at different orientations. In certain embodiments, the system also includes a phoropter module and an output module. The phoropter module is configured to perform a subjective refraction for determining a plurality of subjective spherical powers based on the plurality of objective prescriptions from the computation module. The plurality of subjective spherical powers includes a first subjective spherical power $f_{s1}$ and a second subjective spherical power $f_{s2}$. The phoropter module has a plurality of spherical lenses and cylindrical lenses, where control of the cylindrical lenses is based only on the plurality of objective prescriptions. The subjective refraction requires subjective feedback from the tested subject reading a chart through the phoropter module. The output module is configured to generate a plurality of prescriptions for eyeglasses from the plurality of objective prescriptions and the subjective refraction. The plurality of prescriptions includes (a) a first prescription having the first subjective spherical power $f_{s1}$, the first objective cylinder power $F_{c1}$, and the first objective cylinder angle $F_{a1}$, and (b) a second prescription having the second subjective spherical power $f_{s2}$, the second objective cylinder power $F_{c2}$, and the second objective cylinder angle $F_{a2}$.

In some embodiments, a system for determining refractive prescription of eyeglasses includes an input device module, a computation module, a phoropter module and an output module. The input device module is configured to receive a refractive data set of an eye of a tested subject. The computation module is configured to generate a plurality of initial prescriptions for the eye from the refractive data set, where the plurality of initial prescriptions includes (i) a first initial prescription having a first initial spherical power $F_{s1}$, a first initial cylinder power $F_{c1}$, and a first initial cylinder angle $F_{a1}$, and (ii) a second initial prescription having a second initial spherical power $F_{s2}$, a second initial cylinder power $F_{c2}$, and a second initial cylinder angle $F_{a2}$. The first initial cylinder power $F_{c1}$ and the first initial cylinder angle Fai of the first initial prescription are optimized for image quality, and the second initial cylinder power $F_{c2}$ and the second initial cylinder angle $F_{a2}$ of the second initial prescription are determined for a reduced image quality compared to that of the first initial prescription, or for obtaining reduced magnification differences at different orientations. The phoropter module is configured to perform a subjective refraction for determining a plurality of subjective spherical powers based on the plurality of initial prescriptions. The plurality of subjective spherical powers includes a first subjective spherical power $f_{s1}$ and a second subjective spherical power $f_{s2}$. The phoropter has a plurality of spherical lenses and cylindrical lenses, where control of the cylindrical lenses is based only on the plurality of initial prescriptions. The subjective refraction requires subjective feedback from the tested subject reading a chart through the phoropter. The output module is configured to generate a plurality of prescriptions for eyeglasses from the plurality of objective prescriptions and the subjective refraction, the plurality of prescriptions including (a) a first prescription having the first subjective spherical power $f_{s1}$, the first initial cylinder power $F_{c1}$, and the first initial cylinder angle $F_{a1}$, and (b) a second prescription having the second subjective spherical power $f_{s2}$, the second initial cylinder power $F_{c2}$, and the second initial cylinder angle $F_{a2}$.

In some embodiments, a system for determining refractive prescription of eyeglasses includes an input device module, a phoropter module and an output module. The input device module is configured to receive a plurality of initial prescriptions. The plurality of initial prescriptions includes (i) a first initial prescription having a first initial spherical power $F_{s1}$, a first initial cylinder power $F_{c1}$, and a first initial cylinder angle $F_{a1}$, and (ii) a second initial prescription having a second initial spherical power $F_{s2}$, a second initial cylinder power $F_{c2}$, and a second initial cylinder angle $F_{a2}$. The phoropter module is configured to perform a subjective refraction for determining a plurality of subjective spherical powers based on the plurality of initial prescriptions. The plurality of subjective spherical powers includes a first subjective spherical power $f_{s1}$ and a second subjective spherical power $f_{s2}$. The phoropter module includes a plurality of spherical lenses and cylindrical lenses, where control of the cylindrical lenses is based only on the plurality of initial prescriptions. The subjective refraction requires subjective feedback from the tested subject reading a chart through the phoropter module. The output module is configured to generate a plurality of prescriptions for eyeglasses from the plurality of initial prescriptions and the subjective refraction, the plurality of prescriptions including (a) a first prescription having the first subjective spherical power $f_{s1}$, the first initial cylinder power $F_{c1}$, and the first initial cylinder angle $F_{a1}$, and (b) a second prescription having the second subjective spherical power $f_{s2}$, the second initial cylinder power $F_{c2}$, and the second initial cylinder angle $F_{a2}$.

DETAILED DESCRIPTION OF THE EMBODIMENTS

Reference now will be made in detail to embodiments of the disclosed invention, one or more examples of which are illustrated in the accompanying drawings. Each example is provided by way of explanation of the present technology, not as a limitation of the present technology. In fact, it will be apparent to those skilled in the art that modifications and variations can be made in the present technology without departing from the scope thereof. For instance, features illustrated or described as part of one embodiment may be used with another embodiment to yield a still further embodiment. Thus, it is intended that the present subject matter covers such modifications and variations as come within the scope of the appended claims and their equivalents.

Figure 2:
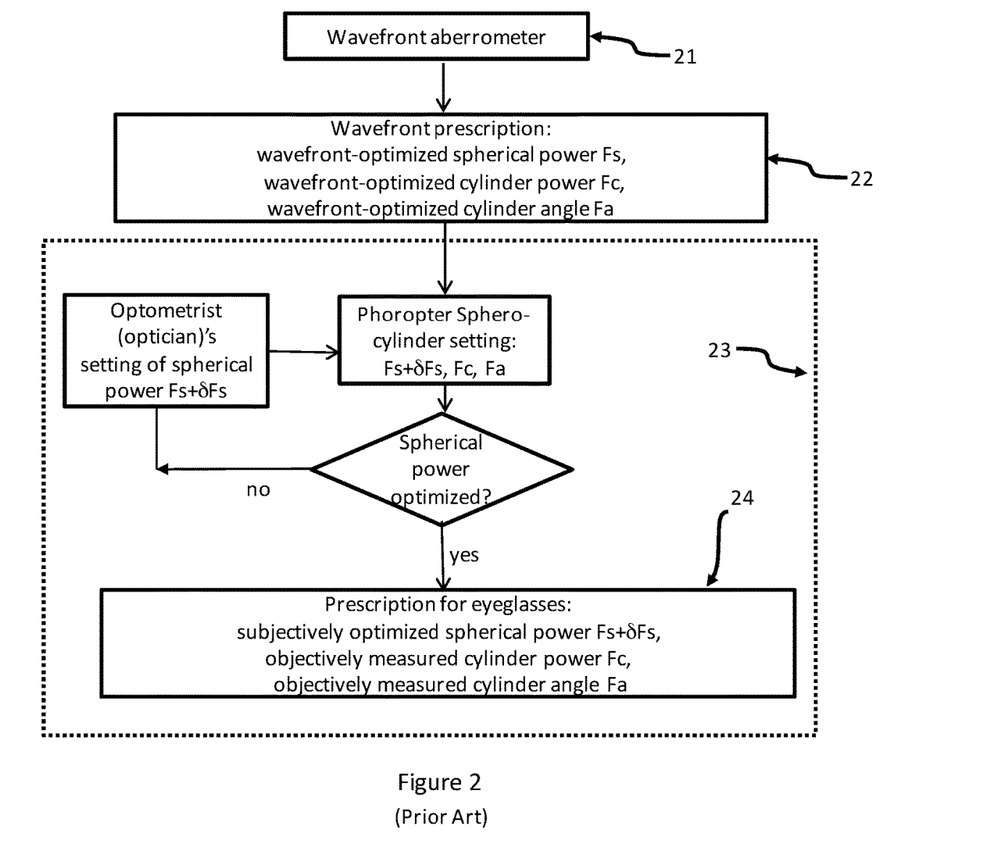
FIG. 2 shows a flowchart for a wavefront method used for determining refractive prescription of eyeglasses known in the art.

FIG. 2 shows a recently developed method for customized refractive correction based on wavefront measurement, related to methods described in U.S. Pat. Nos. 8,419,185, 8,827,448, and U.S. application Ser. No. 14/465,755 entitled "Methods and Devices for Refractive Correction of Eyes," all of which are incorporated herein by reference. First, a wavefront aberrometer 21 is used to measure all refractive errors of an eye. A wavefront aberrometer is more accurate than a conventional autorefractor because it uses a wavefront sensor to precisely measure not only the focus error and astigmatism (a cylinder power and a cylinder angle), but also other higher order aberrations such as coma, spherical aberration, and all the other irregular aberrations in an eye. Second, a wavefront prescription 22 is generated for the tested eye with a wavefront-optimized spherical power $F_s$, a wavefront-optimized cylinder power $F_c$, and a wavefront-optimized cylinder angle $F_a$. Because of the high accuracy of the wavefront sensor as well as wavefront optimization with all the higher-order aberrations, the wavefront-optimized cylinder power $F_c$ and the wavefront-optimized cylinder angle $F_a$ of the eye are thus finalized with the wavefront refraction. Third, a phoropter 23 is used for a subjective optimization. Operators (e.g., optometrists or opticians) set the phoropter according to the objective wavefront refraction, and ask the tested subjects (patients) to subjectively optimize the spherical power. With the tested subject viewing an acuity chart, an optical professional (which shall also be used interchangeably with the terms optometrist or optician for the purposes of this disclosure) will modify the spherical power based on feedback of the patient being tested. The same process is repeated for the other eye of the tested subject. Third, the final prescription 24 of the eyeglasses is determined for each eye with the subjectively optimized spherical power $F_s$, the wavefront optimized cylinder power $F_c$, and the wavefront optimized cylinder angle $F_a$.

The wavefront method in FIG. 2 does improve vision beyond the conventional refraction in FIG. 1. However, similar to the conventional subjective refraction in FIG. 1, it is a different matter whether the tested subject will like the improved vision with the pair of wavefront-customized eyeglasses.

Lenses of eyeglasses are usually 12.5 mm in front of the corneal vertex of human eyes while the nodal points of human eyes are about 7 mm behind the corneal vertex in human anatomy. This distance from lenses to the nodal points of 19.5 mm leads to demagnification of retinal images for negative lenses (myopia correction) and magnification of retinal images for positive lenses (hyperopia correction) with the eyeglasses. Toric lenses with cylinder powers in eyeglasses having different refractive power in the two principal meridians will cause a magnification difference in the two principal meridians, and leads to image distortion of eyeglasses. This image distortion cannot be detected in the refraction process because the size of acuity chart letters is too small for the tested subjects to notice the image distortion, but can have significant impact on the experience of new eyeglasses for consumers.

This problem of image distortion certainly not only is unable to be addressed with the wavefront refraction technique in FIG. 2 in the prior art, but also cannot be handled by the conventional refraction technique in FIG. 1 as well.

The conventional refraction process as shown in FIG. 1 relies on the experience and skills of an individual optometrist (optician) to set the starting as well as the ending cylinder power for the eyeglasses. This conventional approach has at least three drawbacks. First, the process, relying on the experience of an optical professional, is not scientific and thus optimized results are usually not obtained. Second, the process cannot be standardized because each optical professional has his/her own experience in the past, which will also change over time for each optical professional. Third, the process does not take into account individual tolerance of image distortion, and people get a "one size fits all" solution by an individual optometrist or optician even though this certainly should not be.

The present disclosure includes methods and systems for reducing or eliminating image distortion of eyeglasses.

Figure 3:
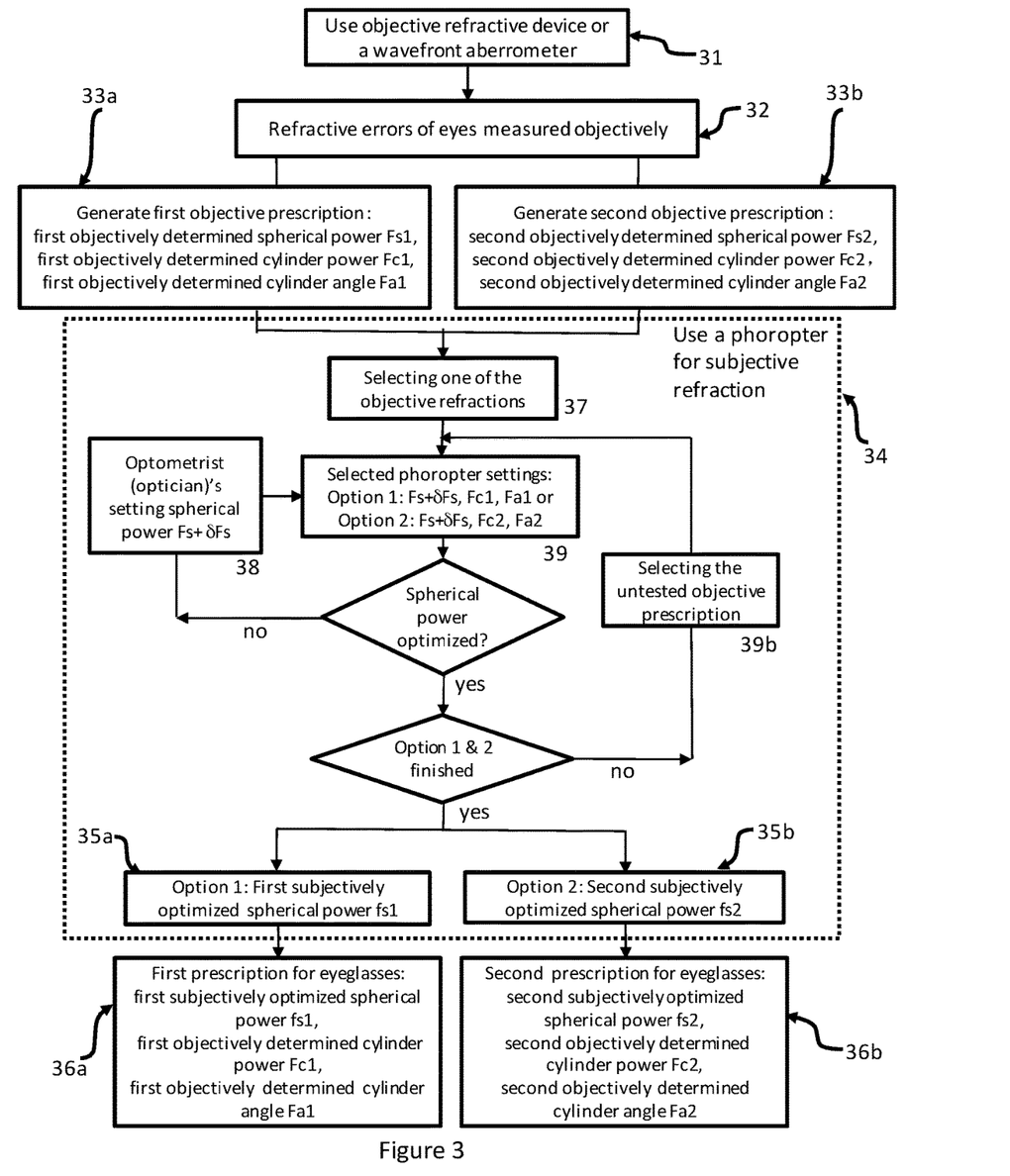
FIG. 3 shows a flowchart for an improved method for determining refractive prescription of eyeglasses in accordance with some embodiments.

In one embodiment, an improved method for determining refractive prescription for eyeglasses is described as shown in FIG. 3.

In the first step 31 of FIG. 3, an objective refraction device is used to measure refractive errors of a human eye objectively. The objective refraction device, which excludes— that is, does not involve—subjective feedback from the tested subject, should provide accurate and objective measurement of refractive errors of eyes 32. The refractive errors may include a focus error, a cylinder error, a cylinder power, coma, and spherical aberration in an eye. In the second step 33a/33b, a plurality of objective prescriptions is generated from the refractive errors of a human eye measured objectively. In one embodiment, a plurality of objective prescriptions includes at least a first objective prescription 33a having a first objectively determined spherical power $F_{s1}$, a first objectively determined cylinder power $F_{c1}$, and a first objectively determined cylinder angle $F_{a1}$; and a second objective prescription 33b having a second objectively determined spherical power $F_{s2}$, a second objectively determined cylinder power $F_{c2}$, and a second objectively determined cylinder angle $F_{a2}$. In one embodiment, the first objective prescription is optimized for image quality—e.g., to offer the best image quality—while the second objective prescription is determined for a reduced image quality compared to that of the first objective prescription, or for obtaining reduced magnification differences at different orientations. In some embodiments, more than two objective prescriptions 33a, 33b may be generated.

In the third step of FIG. 3, a phoropter 34 (which may also be referred to as a phoropter module in this disclosure) is used to perform subjective refraction, to determine a plurality of subjective spherical powers subjectively. In one embodiment, a plurality of subjective spherical powers includes at least a first subjectively-optimized spherical error $f_{s1}$ (35a), and a second subjectively-optimized spherical power $f_{s2}$ (35b). Note that the term spherical power is also known in the industry as focus power. The phoropter 34, placed in front of the eyes of the test subjects to see through so that different correction lenses can be selected for the correction of focus error as well as cylinder error, includes a plurality of spherical lenses and cylindrical lenses. The test subject, seeing through the lenses in the phoropter, provides feedback about what he/she can recognize on an acuity chart. The operator (a optometrist or an optician) is only allowed to change the spherical power of the phoropter and to switch between the objective prescriptions previously generated prior to step 34. Control of cylinder lenses in the phoropter is based only on the plurality of objective prescriptions generated automatically (e.g., 33a, 33b), and the cylinder lenses are prohibited from being changed by the operator. That is, when using the phoropter in step 34, sub-step 37 involves selecting one of the objective refractions 33a or 33b. The optical professional provides a spherical power setting in sub-step 38. The phoropter thus can present to the patient two options in sub-step 39: option 1 using the objective cylinder power $F_{c1}$ and objective cylinder angle $F_{a1}$ with the spherical power $F_s+\delta F_s$ ($\delta$ representing an adjustment made in the subjective assessment), or option 2 using the objective cylinder power $F_{c2}$ and objective cylinder angle $F_{a2}$ with the spherical power $F_s+\delta F_s$. Before the spherical power is subjectively optimized, the spherical power is adjusted in sub-step 38 and the subjective assessment is repeated using the settings indicated in sub-step 39 until the spherical power is optimized for the prescription option (option 1 or 2) that is being assessed. After the spherical power assessment for one option has been completed, the other untested prescription is selected in sub-step 39b and the process is repeated. Once the spherical power has been subjectively optimized for both option 1 and option 2, option 1 and option 2 are finished, with option 1 resulting in the first subjectively-optimized spherical error $f_{s1}$ (35a) and option 2 resulting in the second subjectively-optimized spherical power $f_{s2}$ (35b).

In the fourth step of FIG. 3, a plurality of prescriptions for eyeglasses is generated including at least a first prescription for eyeglasses 36a with a first subjective spherical power $f_{s1}$, a first objective cylinder power $F_{c1}$, and a first objective cylinder angle $F_{a1}$; and a second prescription 36b with a second subjective spherical power $f_{s2}$, a second objective cylinder power $F_{c2}$, and a second objective cylinder angle $F_{a2}$. In some embodiments, more than two prescriptions for eyeglasses 36a, 36b can be generated. These prescriptions for eyeglasses can then be utilized to help a patient select the optimal choice for reducing or eliminating image distortion.

In one aspect of this embodiment, the method further includes generating a final prescription for eyeglasses according to a final preference given by the tested subject. Eyeglasses according to the plurality of prescriptions are realized by a plurality of the trial lenses presented on one or more eyeglass frames, which are worn on the face of the tested subject. From wearing the trial lenses, the tested subject can then select their final preference for which prescription for eyeglasses provides the best vision.

The improved method of FIG. 3 overcomes the three drawbacks of the conventional process shown in FIG. 1. First, the improved method according to the present disclosure does not rely on experience of optical professionals to handle issues of image distortion, and actually does not allow optometrists/opticians to change the cylinder powers and cylinder angles based on their experience and skills. This makes the refraction process standardized. Second, instead of obtaining only a "one solution fits all" prescription in the conventional process by optometrists or opticians as in FIG. 1 and wavefront customized prescription in FIG. 2, the improved method provides at least two different solutions that are different for the effect of image distortion. This allows the individual consumer to find the best eyeglasses without noticing image distortion. This solves the problem of individual difference in tolerance of image distortion. Third, the improved method can provide objectively optimized results based on scientific calculation. Differences in cylinder power or cylinder angle in a plurality of prescriptions are objectively determined based on a number of factors including but not limited to 1) ratio of the spherical power to the cylinder power for an eye according to refractive errors of an eye measured objectively, which allows automatic and precise calculation of a ratio of magnification in each prescription by a person of ordinary skill in the art, and provides solutions with different levels of image distortion; 2) the relationship between coma and cylinder power and cylinder angle in an eye; 3) absolute value of cylinder power according to refractive errors of eye measured objectively; 4) absolute value of cylinder angle according to refractive errors of an eye measured objectively; 5) the relationship between cylinder angles in both eyes of the same tested subjects because the final image distortion of a pair of eyeglasses will be determined by perception by both eyes through a pair eyeglasses; and 6) the cylinder power and cylinder angle of a pair of old eyeglasses worn previously by the tested subject, which represents the prior level of image distortion that has been experienced by the tested subject.

In some embodiments, the objective refraction device involves measuring wavefront aberration of an eye, and the wavefront aberration includes coma and spherical aberration in the eye.

In some embodiments, a plurality of objective prescriptions generated are different in cylinder power, and/or are different in cylinder angle. For example, the first objective cylinder power $F_{c1}$ and the second objective cylinder power $F_{c2}$ are different from each other. In other embodiments, the first objective cylinder angle $F_{a1}$ and the second objective cylinder angle $F_{a2}$ are different from each other.

In some embodiments, the method is further configured to take into account refraction data for the left and right eyes of the tested subject, or refraction data of an old pair of eyeglasses worn by the tested subject before.

In some embodiments, the final prescription for eyeglasses further includes a spherical aberration.

In yet other aspects, the methods in the present disclosure includes an information processing method for a system for determining refractive prescription of eyeglasses.

Figure 4:
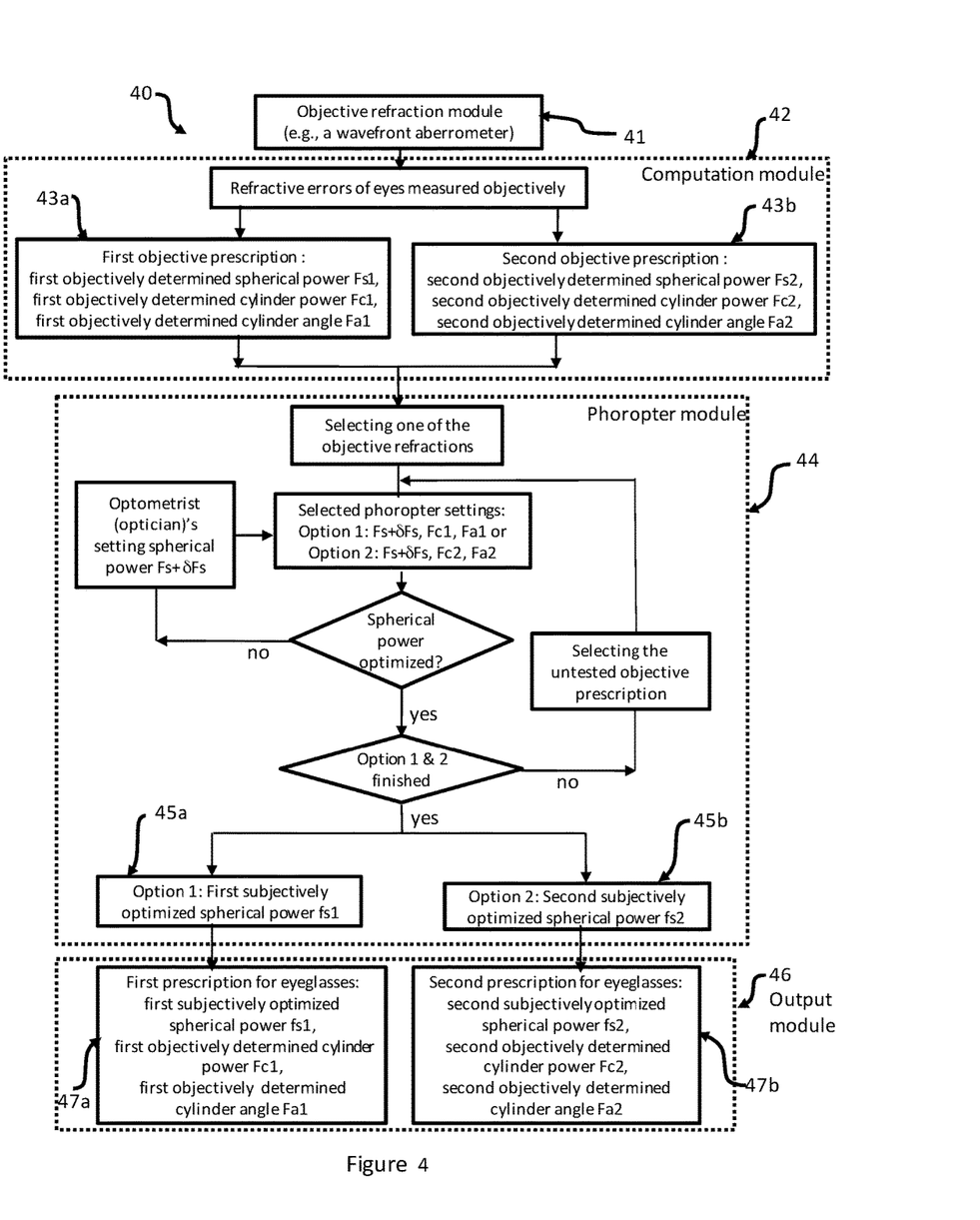
FIG. 4 shows a block diagram of an improved system for determining refractive prescription of eyeglasses in accordance with some embodiments.

FIG. 4 shows a block diagram of an embodiment of a system 40 used for implementing the improved method in FIG. 3, for determining refractive prescription of eyeglasses for human subjects. The system 40 comprises a module of objective refraction 41 that measures refractive errors of a human eye objectively. Objective measurement does not involve any subjective feedback of the tested subject. The objective refraction module or device 41 can be, for example, a wavefront aberrometer that measures all aberrations of an eye including a focus error, a cylindrical error, a cylinder angle, spherical aberration and coma in an eye. In some embodiments, objective refraction device 41 can also be an improved autorefractor that is capable of precisely measuring the focus error and cylinder error of an eye. System 40 also includes a computation module 42 that generates a plurality of objective prescriptions from the refractive errors of a human eye measured objectively. In one embodiment, the plurality of objective prescriptions includes at least a first objective prescription 43a with a first objective spherical power $F_{s1}$, a first objective cylinder power $F_{c1}$, and a first objective cylinder angle $F_{a1}$; and a second objective prescription 43b with a second objective spherical power $F_{s2}$, a second objective cylinder power $F_{c2}$, a second objective cylinder angle $F_{a2}$. In one embodiment, the first objective prescription 43a is optimized for image quality, such as to offer the best image quality, while the second objective prescription 43b is determined for a reduced image quality compared to that of the first objective prescription, or for obtaining reduced magnification differences at different orientations.

System 40 also includes a phoropter module 44 that utilizes the plurality of objective prescriptions 43a, 43b from the computation module 42. Phoropter module 44 is configured to perform a subjective refraction, for determining a plurality of subjective spherical powers subjectively based on the plurality of objective prescriptions. In one embodiment, a plurality of subjective spherical powers include at least a first subjective spherical power 45a ($f_{s1}$), and a second subjective spherical power 45b ($f_{s2}$). The phoropter 44, which includes a plurality of spherical lenses and cylindrical lenses and control of the cylinder lenses, is placed in front of eyes of the test subject to see through so that different correction lenses can be selected for the correction of focus error as well as cylinder error in an eye. Test subjects see through the lenses in the phoropter and provide feedback about what he/she can recognize on a chart such as an acuity chart. The operator (a optometrist, optician, or even the tested subject) is only allowed to change spherical power of the phoroptor. Control of cylinder lenses in the phoropter is based on the plurality of objective prescriptions generated automatically only, and is prohibited from being changed by an operator. The subjective refraction requires subjective feedback of the tested subject reading a chart through the phoropter and providing subjective feedback.

System 40 also includes an output module 46 for generating a plurality of prescriptions for eyeglasses including at least a first prescription 47a and a second prescription 47b. First prescription includes subjective spherical power $f_{s1}$, first objective cylinder power $F_{c1}$, and first objective cylinder angle $F_{a1}$. Second prescription 47b includes second subjective spherical power $f_{s2}$, second objective cylinder power $F_{c2}$, and second objective cylinder angle $F_{a2}$.

In some embodiments, the objective refraction device 41 involves measuring wavefront error of an eye using a lens array wavefront sensor.

In some embodiments, the plurality of objective prescriptions 43a, 43b that are generated are different in cylinder power, and/or are different in cylinder angle.

In some embodiments, the prescriptions for eyeglasses 47a and 47b of system 40 is further configured to take into account refraction data for a left eye and a right eye of the tested subject, or refraction data of old eyeglasses worn by the tested subject before.

In some embodiments, the final prescriptions 47a, 47b for eyeglasses further include a spherical aberration.

Figure 5:
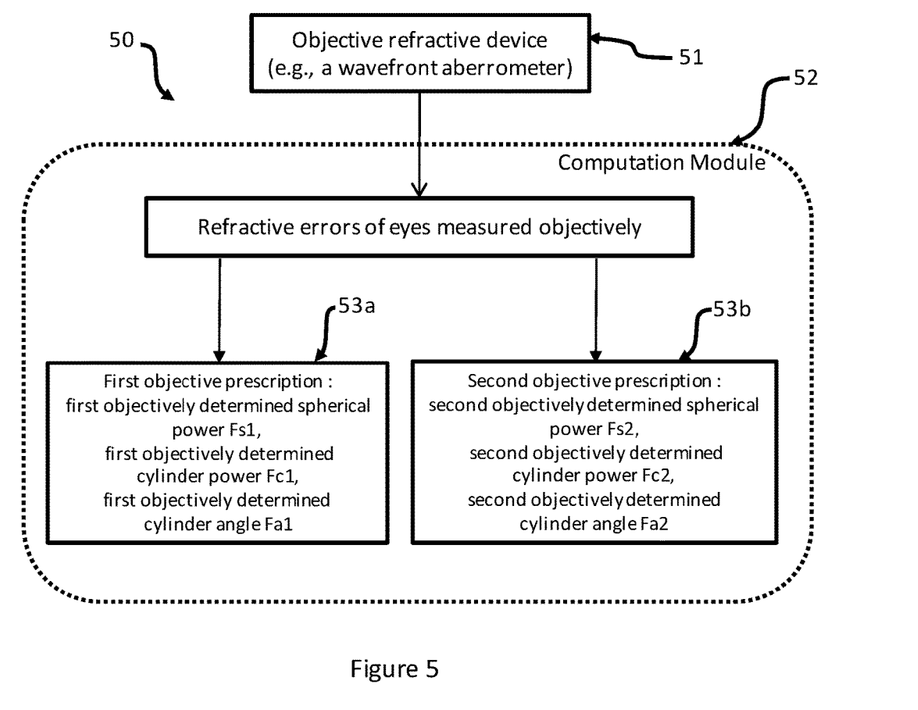
FIG. 5 shows a block diagram of an improved system for determining refractive prescription of eyeglasses in another embodiment of the present disclosure.

In yet another embodiment, FIG. 5 shows a block diagram of a system 50 for generating the plurality of objective prescriptions. System 50 is a sub-system of FIG. 4, for determining refractive prescription of eyeglasses for human subjects. The system 50 includes a module of objective refraction 51 that measures refractive errors of a human eye objectively, and a computation module 52. Objective measurement does not involve any subjective feedback of the tested subject. The objective refraction device 51 can be, for example, a wavefront aberrometer that measures all aberrations of an eye including focus error, cylindrical error, spherical aberration and coma. Objective refraction device 51 can also be an improved autorefractor that is capable of precisely measuring focus error and cylinder error. System 50 also includes a computation module 52 that generates a plurality of objective prescriptions from the refractive errors of a human eye measured objectively by objective refraction device 51. In one embodiment, a plurality of objective prescriptions includes at least a first objective prescription 53a and a second objective prescription 53b. First objective prescription 53a has a first objective spherical power $F_{s1}$, a first objective cylinder power $F_{c1}$, and a first objective cylinder angle $F_{a1}$. Second objective prescription 53b has a second objective spherical power $F_{s2}$, a second objective cylinder power $F_{c2}$, and a second objective cylinder angle $F_{a2}$.

In some aspects of this embodiment, the plurality of objective prescriptions 53a, 53b that are generated are different in cylinder power, and/or are different in cylinder angle.

In some aspects of this embodiment, the plurality of objective prescriptions 53a and 53b of system 50 is further configured to take into account refraction data for the left and right eyes of the tested subject, or refraction data of eyeglasses previously worn by the tested subject.

In some aspects of this embodiment, the plurality of objective prescriptions 53a, 53b further include a spherical aberration.

In some aspects of this embodiment, the system 50 is further configured to be combined with a phoropter module for subjective refinement of a plurality of objective prescriptions, particularly for the subjective refinement (refraction) of the spherical powers.

Figure 6:
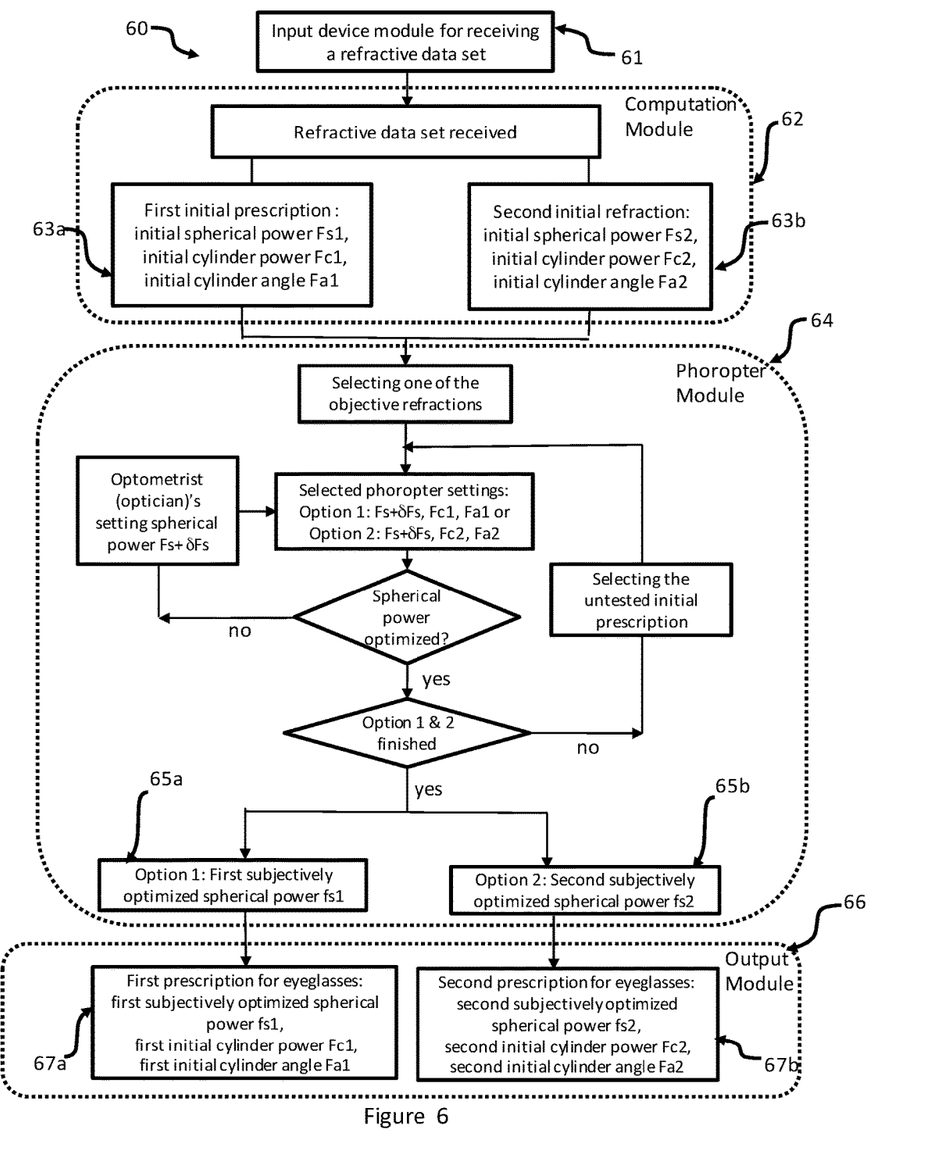
FIG. 6 shows a block diagram of an improved system for determining refractive prescription of eyeglasses in yet another embodiment of the present disclosure.

In yet another embodiment, FIG. 6 shows a system 60 in which an input device is used for receiving refractive data for eyes. System 60 is a modified sub-system of FIG. 4 as well, for determining refractive prescription of eyeglasses for human subjects. The system 60 includes an input device module 61 configured to receive a refractive data set of an eye, the refractive data set including at least an input spherical power, an input cylinder power and an input cylinder angle, and may also include coma and spherical aberration in the eye. A computation module 62 of system 60 generates a plurality of initial prescriptions from the received refractive data set of an eye. In one embodiment, a plurality of initial prescriptions generated from the received refractive data set includes at least a first and a second initial prescription 63a and 63b. First initial prescription 63a has a first initial spherical power $F_{s1}$, a first initial cylinder power $F_{c1}$, and a first initial cylinder angle $F_{a1}$. Second initial prescription 63b has a second initial spherical power $F_{s2}$, a second initial cylinder power $F_{c2}$, and a second initial cylinder angle $F_{a2}$. In one embodiment, the first initial prescription is optimized for image quality, such as to offer the best image quality, while the second initial prescription is determined for a reduced image quality when compared to that of the first initial prescription, or for obtaining reduced magnification differences at different orientations. In some embodiments, more than two initial prescriptions 63a and 63b may be generated.

A phoropter module 64 takes the plurality of initial prescriptions (e.g., 63a and 63b) from the computation module 62. Phoropter module 64 is configured for determining a plurality of spherical powers subjectively. In one embodiment, a plurality of subjective spherical powers includes at least a first subjective spherical power 65a $f_{s1}$, and a second subjective spherical power 65b $f_{s2}$. The phoropter 64, placed in front of the eyes of the test subject to see through so that different correction lenses can be selected for the correction of focus error as well as cylinder error in an eye, contains of a plurality of spherical lenses and cylindrical lenses. The test subject, seeing through the lenses in the phoropter, provides feedback about what he/she can recognize on an acuity chart. The operator (a optometrist or an optician) is only allowed to change the spherical power of the phoropter. Control of cylinder lenses in the phoropter is based only on the plurality of objective prescriptions generated automatically, and is prohibited from being changed by an operator.

System 60 also includes an output module 66 for generating a plurality of prescriptions for eyeglasses, the plurality of prescriptions including at least a first prescription 67a with the subjective spherical power $f_{s1}$, the first initial cylinder power $F_{c1}$, and the first initial cylinder angle $F_{a1}$. The plurality of prescriptions for eyeglasses also includes at least a second prescription 67b with the second subjective spherical power $f_{s2}$, the second initial cylinder power $F_{c2}$, and the second initial cylinder angle $F_{a2}$. As in previous embodiments, the plurality of prescriptions may include more than two prescriptions 67a, 67b.

In some aspects of this embodiment, the input device module 61 includes but is not limited to one of the following: a keyboard, a touch screen, or a touch-free electronic communication from another device.

In some aspects of this embodiment, a plurality of initial prescriptions 63a and 63b that are generated are different in cylinder power, and/or are different in cylinder angle.

In some aspects of this embodiment, the prescriptions for eyeglasses 67a and 67b take into account refraction data for the left and right eyes of the tested subject, or refraction data of an old set of eyeglasses worn previously by the tested subjects.

In some aspects of this embodiment, the plurality of prescriptions for eyeglasses 67a and 67b further include a spherical aberration in an eye.

Figure 7:
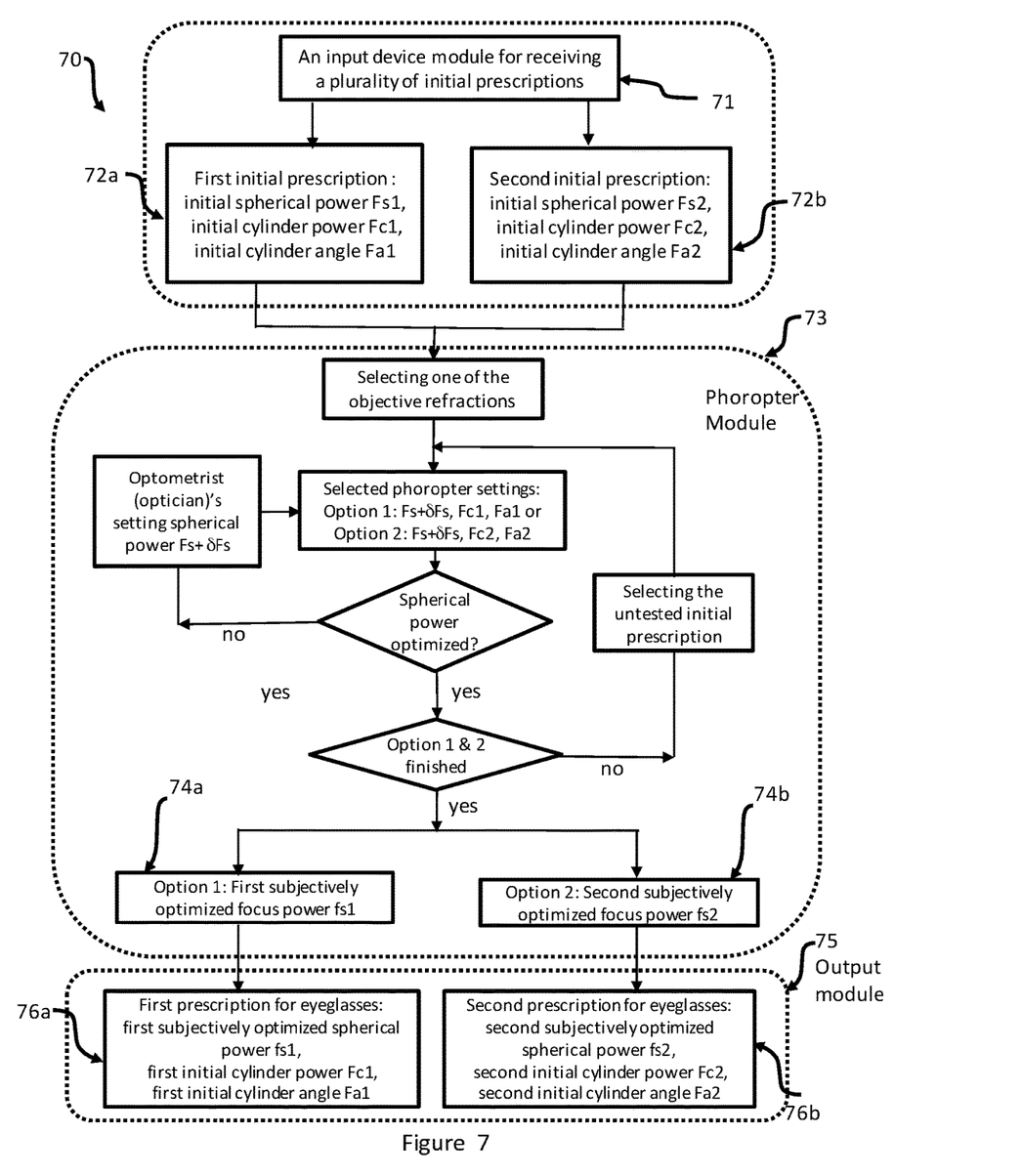
FIG. 7 shows a block diagram of an improved system for determining refractive prescription of eyeglasses in still another embodiment of the present disclosure.

In still another embodiment, FIG. 7 shows a system 70 for determining refractive prescription of eyeglasses for human subjects. The system includes an input device module 71 that is configured to receive a plurality of initial prescriptions. In one embodiment, the plurality of initial prescriptions includes at least a first initial prescription 72a with a first initial spherical power $F_{s1}$, a first initial cylinder power $F_{c1}$, and a first initial cylinder angle $F_{a1}$; and a second initial prescription 72b with a second initial spherical power $F_{s2}$, a second initial cylinder power $F_{c2}$, and a second initial cylinder angle $F_{a2}$. System 70 includes a phoropter module 73 that receives the plurality of initial prescriptions 72a, 72b from the input device module 71.

Phoropter module 73 is configured for determining a plurality of subjective spherical powers subjectively; that is, to perform a subjective refraction. In one embodiment, a plurality of subjective spherical powers includes at least a first subjective spherical power 74a ($f_{s1}$), and a second subjective spherical power 74b ($f_{s2}$). The phoropter 73, placed in front of eyes of the test subject to see through so that different correction lenses can be selected for the correction of focus error as well as cylinder error in an eye, contains a plurality of spherical lenses and cylindrical lenses. The test subject, seeing through the lenses in the phoropter, provides feedback about what he/she can recognize on an acuity chart. The operator (a optometrist or an optician) is only allowed to change the spherical power of the phoroptor, by adjusting the spherical lenses. Control of cylinder lenses in the phoropter is based on the plurality of objective prescriptions generated automatically only, and is prohibited from being changed by the operator.

An output module 75 generates a plurality of prescriptions for eyeglasses including at least a first prescription 76a with the subjective spherical power $f_{s1}$, the first initial cylinder power $F_{c1}$, and the first initial cylinder angle $F_{a1}$; and a second prescription 76b with the second subjective spherical power $f_{s2}$, the second initial cylinder power $F_{c2}$, and the second initial cylinder angle $F_{a2}$.

In some aspects of this embodiment, the input device 71 includes but is not limited to one of the following: a keyboard, a touch screen, or a touch-free electronic communication from another device.

In some aspects of this embodiment, the prescriptions for eyeglasses 76a and 76b take into account refraction data for the left and right eyes of the tested subject. The prescriptions for eyeglasses 76a and 76b may also take into account refraction data of an old pair of eyeglasses worn by the tested subject before.

In some aspects of this embodiment, the plurality of prescriptions 76a, 76b for eyeglasses further includes spherical aberration in the eye.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those skilled in the art, without departing from the scope of the present invention, which is more particularly set forth in the appended claims. Furthermore, those skilled in the art will appreciate that the foregoing description is by way of example only, and is not intended to limit the invention.

What is claimed is:

1. A method for determining refractive prescription for eyeglasses, the method comprising:
using an objective refraction device to measure refractive errors of an eye of a tested subject objectively, wherein the objective refraction device excludes subjective feedback from the tested subject;
generating a plurality of objective prescriptions for the tested subject from the refractive errors of the eye measured objectively, wherein:
the plurality of objective prescriptions comprises (i) a first objective prescription having a first objective spherical power $F_{s1}$, a first objective cylinder power $F_{c1}$, and a first objective cylinder angle $F_{a1}$, and (ii) a second objective prescription having a second objective spherical power $F_{s2}$, a second objective cylinder power $F_{c2}$, and a second objective cylinder angle $F_{a2}$; and
the first objective cylinder power $F_{c1}$ and the first objective cylinder angle $F_{a1}$ of the first objective prescription are optimized for image quality, and the second objective cylinder power $F_{c2}$ and the second objective cylinder angle $F_{a2}$ of the second objective prescription are determined for a reduced image quality compared to that of the first objective prescription, or for obtaining reduced magnification differences at different orientations;
using a phoropter to perform a subjective refraction to determine a plurality of subjective spherical powers, wherein the plurality of subjective spherical powers comprises a first subjective spherical power $f_{s1}$ and a second subjective spherical power $f_{s2}$;
wherein the phoropter comprises a plurality of spherical lenses and cylindrical lenses,
wherein control of the cylindrical lenses is based only on the plurality of objective prescriptions; wherein the subjective refraction requires subjective feedback from the tested subject reading a chart through the phoropter; and
generating a plurality of prescriptions for eyeglasses from the plurality of objective prescriptions and the subjective refraction, the plurality of prescriptions for eyeglasses comprising (a) a first prescription having the first subjective spherical power $f_{s1}$, the first objective cylinder power $F_{c1}$, and the first objective cylinder angle $F_{a1}$, and (b) a second prescription having the second subjective spherical power $f_{s2}$, the second objective cylinder power $F_{c2}$, and the second objective cylinder angle $F_{a2}$.

2. The method of claim 1 further comprising generating a final prescription for eyeglasses according to a final preference given by the tested subject, the final preference being based on the tested subject wearing trial lenses according to the generated plurality of prescriptions for eyeglasses.

3. The method of claim 2 wherein the final prescription for eyeglasses further comprises a spherical aberration.

4. The method of claim 1 wherein the using the objective refraction device comprises measuring a wavefront error of the eye, wherein the wavefront error includes coma and spherical aberration in the eye.

5. The method of claim 1 wherein the first objective cylinder power and the second objective cylinder power are different from each other.

6. The method of claim 5 wherein the plurality of prescriptions for eyeglasses takes into account at least one of (i) refraction data for a left eye and a right eye of the tested subject, and (ii) refraction data of eyeglasses previously worn by the tested subject.

7. The method of claim 1 wherein the first objective cylinder angle and the second objective cylinder angle are different from each other.

8. The method of claim 7 wherein the plurality of prescriptions for eyeglasses takes into account at least one of (i) refraction data for a left eye and a right eye of the tested subject, and (ii) refraction data of eyeglasses previously worn by the tested subject.

9. A system for determining refractive prescription of eyeglasses, comprising:
an objective refraction module configured to measure refractive errors of an eye of a tested subject objectively, wherein the objective refraction module excludes subjective feedback from the tested subject; and
a computation module configured to generate a plurality of objective prescriptions for the tested subject from the refractive errors of the eye measured objectively, wherein:
the plurality of objective prescriptions comprises (i) a first objective prescription having a first objective spherical power $F_{s1}$, a first objective cylinder power $F_{c1}$, and a first objective cylinder angle $F_{a1}$, and (ii) a second objective prescription having a second objective spherical power $F_{s2}$, a second objective cylinder power $F_{c2}$, and a second objective cylinder angle $F_{a2}$; and
the first objective cylinder power $F_{c1}$ and the first objective cylinder angle $F_{a1}$ of the first objective prescription are optimized for image quality, and the second objective cylinder power $F_{c2}$ and the second objective cylinder angle $F_{a2}$ of the second objective prescription are determined for a reduced image quality compared to that of the first objective prescription, or for obtaining reduced magnification differences at different orientations.

10. The system of claim 9 wherein the objective refraction module is further configured to measure a wavefront error of the eye, wherein the wavefront error includes coma and spherical aberration in the eye.

11. The system of claim 9 wherein the first objective cylinder power and the second objective cylinder power are different from each other.

12. The system of claim 11 wherein the plurality of prescriptions for eyeglasses takes into account at least one of (i) refraction data for a left eye and a right eye of the tested subject, and (ii) refraction data of eyeglasses previously worn by the tested subject.

13. The system of claim 9 wherein the first objective cylinder angle and the second objective cylinder angle are different from each other.

14. The system of claim 13 wherein the plurality of prescriptions for eyeglasses takes into account at least one of (i) refraction data for a left eye and a right eye of the tested subject, and (ii) refraction data of eyeglasses previously worn by the tested subject.

15. The system of claim 9 wherein the plurality of prescriptions for eyeglasses further comprises a spherical aberration.

16. The system of claim 9 further comprising a phoropter module configured to perform a subjective refraction for determining a plurality of subjective spherical powers based on the plurality of objective prescriptions from the computation module, wherein the plurality of subjective spherical powers comprises a first subjective spherical power $f_{s1}$ and a second subjective spherical power $f_{s2}$; wherein the phoropter module comprises a plurality of spherical lenses and cylindrical lenses, wherein control of the cylindrical lenses is based only on the plurality of objective prescriptions; wherein the subjective refraction requires subjective feedback from the tested subject reading a chart through the phoropter module.

17. The system of claim 16 further comprising an output module configured to generate a plurality of prescriptions for eyeglasses from the plurality of objective prescriptions and the subjective refraction, the plurality of prescriptions comprising (a) a first prescription having the first subjective spherical power $f_{s1}$, the first objective cylinder power $F_{c1}$, and the first objective cylinder angle $F_{a1}$, and (b) a second prescription having the second subjective spherical power $f_{s2}$, the second objective cylinder power $F_{c2}$, and the second objective cylinder angle $F_{a2}$.

18. The system of claim 17 wherein the objective refraction module is further configured to measure a wavefront error of the eye, wherein the wavefront error includes coma and spherical aberration in the eye.

19. The system of claim 17 wherein the first objective cylinder power and the second objective cylinder power are different from each other.

20. The system of claim 19 wherein the plurality of prescriptions for eyeglasses takes into account at least one of (i) refraction data for a left eye and a right eye of the tested subject, and (ii) refraction data of eyeglasses previously worn by the tested subject.

21. The system of claim 17 wherein the first objective cylinder angle and the second objective cylinder angle are different from each other.

22. The system of claim 21 wherein the plurality of prescriptions for eyeglasses takes into account at least one of (i) refraction data for a left eye and a right eye of the tested subject, and (ii) refraction data of eyeglasses previously worn by the tested subject.

23. The system of claim 17 wherein the plurality of prescriptions for eyeglasses further comprises a spherical aberration.

* * * * *